United States Patent [19]

Ladisch

[11] Patent Number: 5,366,963
[45] Date of Patent: Nov. 22, 1994

[54] GANGLIOSIDES WITH IMMUNOSUPPRESSIVE CERAMIDE MOIETIES

[75] Inventor: Stephan Ladisch, Chevy Chase, Md.

[73] Assignee: The Regents of the University of California, Oakland, Calif.

[21] Appl. No.: 21,734

[22] Filed: Feb. 23, 1993

Related U.S. Application Data

[63] Continuation of Ser. No. 738,591, Jul. 31, 1991, abandoned.

[51] Int. Cl.$^5$ ............................................. A61K 31/70
[52] U.S. Cl. ...................................... 514/54; 424/450;
536/4.1; 536/53; 536/55; 536/55.1; 536/55.2;
514/53; 514/61
[58] Field of Search .............................. 514/54, 53, 61;
536/4.1, 53, 55, 55.1, 55.2; 424/450

[56] References Cited

U.S. PATENT DOCUMENTS

| | | | |
|---|---|---|---|
| 4,388,309 | 6/1983 | Fabricius et al. | 514/12 |
| 4,593,091 | 6/1986 | della Valle et al. | 536/53 |
| 4,639,437 | 1/1987 | della Valle et al. | 514/54 |
| 4,728,641 | 3/1988 | Tubaro et al. | 514/54 |
| 4,730,058 | 3/1988 | Ogawa et al. | 549/211 |
| 4,762,822 | 8/1988 | Ettinger | 514/25 |
| 4,849,413 | 7/1989 | della Valle et al. | 514/54 |
| 4,868,292 | 9/1989 | Yokoyama et al. | 536/18.5 |
| 4,880,572 | 11/1989 | Fujita et al. | 260/404 |
| 4,914,085 | 4/1990 | Ochi | 514/25 |
| 4,918,170 | 4/1990 | Hasegawa et al. | 536/1.1 |
| 4,940,694 | 7/1990 | della Valle et al. | 514/25 |
| 4,990,603 | 2/1991 | Ogawa et al. | 536/17.4 |
| 4,990,604 | 2/1991 | Ogawa et al. | 536/17.2 |

OTHER PUBLICATIONS

Dyatlovitskaya et al; Biochim. Biophys. Acta 907:125–143 (1987).
Bergelson et al; Eur. J. Immunol. 19:1979–1983 (1989).
Grayson et al; Cellular Immunology 139:18–29 (1992).
*The Merck Manual* 16th Edition (1992) pp. 352–357.
Ladisch, Stephan et al., "Aberrant Fatty Acyl ... ", The Journal of Biol. Chem., vol. 264, No. 20, pp. 12097–12105, 1989.
Geisler, Fred H., M.D. et al., "Recovery of Motor Function ... " The New England Jour. of Med., vol. 324, No. 26, Jun. 27, 1991 (pp. 1829–1839).
Westrick, Mary Alice, et al., "Isolation and Characterization of Gangliosides ... ", Cancer Research 43, 5890–5894, Dec. 1988.
Grassi, Fabio et al., "Chemical residues of ganglioside molecules ... " Eur. J. Immunol. 1990.
Gonwa, Thomas Al., et al., "Inhibition of Mitogen–and Antigen–Induced Lymphocyte ... ", Cancer Research 44, pp. 3467–3470 (1984).
Sonnino, Sandro, et al., "Preparation of GM1 ganglioside molecular species ... " Jour. of Lipid Research, vol. 26, 1985, pp. 248–257.
Presti, D. et al., "Lack of suppression by gangliosides of humoral ... ", Jour. of Neurommunology, 22 (1989) pp. 233–239.

(List continued on next page.)

*Primary Examiner*—Ronald W. Griffin
*Attorney, Agent, or Firm*—Poms, Smith, Lande & Rose

[57] ABSTRACT

A method for suppressing immune responses in animals by administering a mixture of gangliosides to the animal where the gangliosides have heterogeneous ceramide structures containing fatty acid portions with carbon chain lengths of 21–30 or less than 18 carbon atoms. Ganglioside mixtures which are homogeneous with respect to the fatty acid portion are also effective immunosuppressive agents when the carbon chain length of the fatty acid portion is less than 18. Compositions containing the above specified ganglioside mixtures are also disclosed.

8 Claims, 8 Drawing Sheets

OTHER PUBLICATIONS

Kiso, Makoto, et al., "Synthesis of 1-O-(N-Acetyl . . . ", J. Carbohydrate Chemistry, 6(3), 411–422 (1987).
Dawson, Glyn, "Glycosphingolipid Function in Cancer", Cancer Cells, Oct. 1990, vol. 2, No. 10, pp. 327–328.
Cavaillon et al; Eur. J. Immunol. 16:1009–1012 (1986).
Ladisch et al; J. Clin. Invest. 79:1879–1882 (Jun. 1987).
Prokazova et al. Eur. J. Biochem. 172:1–6 (1988).
Floutsis et al.; Int. J. Cancer 43:6–9 (1989).
Hachida et al; Transplant Proc. 22(4):1663–1665 (Aug. 1990).
Agarwal et al; J. Immunol. 107(5):1448–1456 (1971).
Miceli et al; ACTA Psychiat. Scand. 55:102–110 (1977).
Yates et al.; Chemical Abstracts 93: 112178r (1980).
Whisler et al; J. Immunol. 125(5): 2106–2111 (1980).
Hakomori; Ann. Rev. Biochem. 50:733–764 (1981).
Ladisch et al.; Cancer Res. 43:3808–3813 (1983).
Ladisch et al.; J. Clin. Invest. 74:2074–2081 (1984).
Sugimoto et al; Carb. Res. 156:C1–C5 (1986).
Nakakuma et al.; FEBS 258:230–232 (1989).

GANGLIOSIDES WITH IMMUNOSUPPRESSIVE CERAMIDE MOIETIES

This is a continuation of copending application(s) Ser. No. 07/738,591 filed on Jul. 31, 1991, now abandoned.

BACKGROUND OF THE INVENTION

1. Field of the Invention

The present invention relates to gangliosides and their use as immunosuppressive agents. More particularly, the present invention relates to the discovery that structure of the ceramide moiety of gangliosides, which can be extremely heterogeneous, is an important determining factor in the immunosuppressive activity of the ganglioside.

2. Description of the Related Art

Although the immune response is often seen as beneficial, in certain circumstances the immune response to an antigen can actually be harmful to the animal in which the immune response occurs. An example where the immune response creates a condition wherein the host is subject to serious pathologic sequelae is in such autoimmune diseases as lupus erythematosus, rheumatoid arthritis, diabetes, and Crohn's disease. In autoimmune diseases, the immune response is directed against host tissues, and therefore use of immunosuppressive agents is a treatment approach.

Another, and one of the most important, areas which often requires substantial immunosuppression is tissue transplantation, where the suppression of the immune response is crucial in order to prevent graft rejection by the host (host versus graft reaction, HVG) and graft rejection of the host (graft versus host rejection, GVH). Typically, the tissue which is grafted is allogeneic, where the inhibition of alloreactive T lymphocytes by immunosuppressive agents is essential to the prevention of allograft rejection. Depending upon the nature of the allograft (i.e. liver, kidney, or bone marrow), the course of immunosuppressive therapy may be relatively brief (months) or may have to be continued indefinitely (years to lifetime). All of the immunosuppressive agents used thus far have significant drawbacks relating either to direct toxicity on other organ systems or to failure to provide "balanced" immunosuppression. The latter problem has two distinct aspects; on one hand inadequate suppression of the immune response can lead to rejection, while on the other hand excessive immunosuppression can allow the development of opportunistic infections and neoplasia. Thus, the need to develop an effective non-toxic immunosuppressive agent which does not cause the above severe complications continues.

At present, multi-drug therapy, including cytotoxic agents, is utilized following organ transplantation. This typically comprises combination therapy, such as with cyclosporin A, azathioprine, and prednisone, the rationale being that each drug acts at a different stage in the immune response and that combination therapy will require lower doses of each individual drug, thus diminishing their dose-related side effects. However, the side effects remain significant while the efficacy of this form of therapy is still not satisfactory. Rejection continues to account for nearly 50% of graft losses in renal transplantation. And, distinguishing rejection from cyclosporin A nephrotoxicity may be difficult.

Another major cause of graft loss is systemic infection, usually by opportunistic infections, which require dose reduction or cessation of immunosuppression, which leads to graft loss. Also, with such combination therapy in transplantation, there has been a significant increase in the incidence of lymphomas (Wilkinson, et al., "Transplantation," 47:293–296, 1989). The chronic failure of immunosuppressive therapy is revealed by the fact that the graft survival rate of 85% at 1 year drops to 67% at 5 years (Kahan, et al., "Am J Kidney Dis," 5:288–295, 1985) in recipients of cadaveric renal transplants receiving triple therapy. Clearly, then the existing immunosuppressive therapy is inadequate. This has stimulated the search for, and development of, new immunosuppressive drugs, and particularly agents that are not directly toxic to either the immune system or to other organ systems. One approach to overcoming the problems associated with present immunosuppressive drugs is the use of biological agents which are actually produced by the animal. An example of such biological agents are the gangliosides.

Gangliosides are a class of glycosphingolipids that have a structure containing a carbohydrate moiety linked to a ceramide. The carbohydrate moiety includes a sugar moiety which has at least one monosaccharide and one or more a sialic acid moiety(s), i.e., sialic acid groups (N-acetyl or N-glycolyl neuraminic acid).

Gangliosides are classified according to the number of monosaccharides contained in the sugar moiety and according to the number of sialic acid groups present. Further classification is dependent upon where and how many sialic acid(s) are bound to the sugar moiety. For example, the international symbol $G_{M1a}$ designates one of the more common gangliosides which has been extensively studied. The subscript, "M" in the symbol indicates that the ganglioside is a monosialoganglioside and "1" indicates that there are four saccharide units present in the carbohydrate moiety. The lower case subscripts "a" "b" or "c" indicate isomers of the particular ganglioside described which differ in the position of the sialic acid(s). The upper case subscripts "D", "T" and "Q" used in the international ganglioside symbols represent disialogangliosides, trisialogangliosides and tetrasialogangliosides, respectively. The subscripts "2", "3" and "4" represent trisaccharide, disaccharide and monosaccharide gangliosides, respectively. The terminal saccharide is the saccharide which is located at the non-reducing end of the carbohydrate moiety which is opposite to the end (reducing end) that is attached to the ceramide moiety.

A number of different gangliosides have been identified. These gangliosides are abundant in nerve tissue and they are especially abundant in brain tissue. Common gangliosides which have been isolated from brain tissue in significant amounts include $G_{D1a}$, $G_{M1}$, $G_{T1b}$ and $G_{D1b}$. Gangliosides have also been synthetically produced. For example, U.S. Pat. No. 4,918,170 discloses the synthesis of $G_{M3}$ and $G_{M4}$.

It is well known that gangliosides are functionally important in the nervous system and it has been claimed that gangliosides are useful in the therapy of peripheral nervous system disorders. Numerous gangliosides and derivatives thereof have been used to treat a wide variety of nervous system disorders including cerebral ischemic strokes and spinal cord injuries. For example, see U.S. Pat. Nos. 4,940,694; 4,937,232; 4,716,223 and Geisler et al., New England J. Med. 324 1829–38 (1991). Gangliosides have also been used to affect the activity of phagocytes (U.S. Pat. No. 4,831,021) and to treat gastrointestinal disease-producing organisms (U.S. Pat. No. 4,762,822).

The use of gangliosides and ganglioside analogues to suppress or otherwise affect the immune system has not yet been investigated nearly as extensively as their use in neurological disorders.

The first report of ganglioside suppression of immune responses in vivo was published twenty years ago by Agarwal and Neter, who discovered inhibition by gangliosides of the primary antibody response to bacterial antigens in mice (Agarwal, et al., J. Immunol., 107:1448-1456, 1971). Recent studies have shown that tumor gangliosides which are shed in vivo enhance tumor formation in mice (Ladisch, et al., J. Clin. Invest., 79.:1879-1882, 1987), a finding confirmed by other laboratories (Alessandri, et al., Cancer Res., 47:4243-4347, 1987; Saha, et al., Int. J. Cancer, 41:432-435, 1988); indirect evidence (Ladisch, et al., J. Clin. Invest., 79:1879-1882, 1987) suggests that this enhancement occurs by an immunologic mechanism. However, a recent investigation into the in vivo immunosuppressive effect of $G_{M1}$ ganglioside or mixed bovine brain gangliosides (mainly $G_{M1}$, $G_{D1a}$, $G_{D1b}$, and $GT_{1b}$) was conducted by Presti, D. et al., (Presti, D. et al. J. Neuroimmunology, 22:233-239, 1989). The study concluded that there was no evidence of a suppressive effect on humoral or cellular immunity exhibited in vivo by the $G_{M1}$ ganglioside or the mixed brain gangliosides.

Synthetic ganglioside analogues in which the sialic acid moiety has been removed, i.e. desialylated gangliosides (otherwise known as neutral glycophingolipids, NGSL), have been suggested for use to suppress graft rejection in organ transplantation (U.S. Pat. No. 4,388,309), but evidence for effectiveness is weak.

In the past, the identification of preferred active ganglioside structures has been made by considering carbohydrate structural characteristics alone. This main emphasis in the investigation of gangliosides upon carbohydrate structure has completely overlooked the potential contribution of ceramide structure to biological activity of gangliosides. It would be desirable, therefore, to determine the role which the ceramide moiety plays in immunosuppression. Further, it would be desirable to establish to what extent heterogeneity of the ceramide moiety influences ganglioside immunosuppressive activity and whether or not any particular ceramide structures are more effective in suppressing the immune system.

SUMMARY OF THE INVENTION

The present invention is based upon the discovery that the ceramide moiety of gangliosides is unexpectedly heterogeneous and that gangliosides containing different ceramide moieties express different degrees of immunosuppressive activity. The ceramide moieties present in gangliosides consist of a long chain base portion and a fatty acid portion. Normal human brain gangliosides contain ceramide moieties wherein the fatty acid portion predominantly consists of carbon chains containing 18 and 20 carbon atoms. In accordance with the present invention, it was discovered that the immunosuppressive activity of gangliosides increases as the heterogeneity of the fatty acid portion increases from that found in normal brain gangliosides. That is, the ganglioside contains increasing proportions of fatty acyl groups having carbon chain lengths of below 18 and above 20.

Another feature of the present invention involves the discovery that gangliosides having carbon chains which are shorter than the fatty acid portion of normal human brain gangliosides are more effective in suppressing the immune response in an animal.

The present invention provides a method for suppressing an immune response in an animal which includes administering to the animal an immunosuppressively effective amount of a ganglioside wherein the ganglioside includes a carbohydrate moiety and a ceramide moiety. The ceramide moiety includes a long chain base portion and a fatty acid portion wherein the fatty acid portion (i) is more heterogeneous than in human brain gangliosides and/or (ii) is substantially enriched in fatty acyl portions containing less than 18 carbon atoms.

As a feature of the present invention, it was discovered that the immunosuppressive activity of the ganglioside is increased when the fatty acid portion is not hydroxylated.

Compositions in accordance with the present invention include physiologically acceptable carriers which contain an immunosuppressive concentration of gangliosides. The compositions are used in accordance with the method of the present invention to treat a wide variety of conditions wherein the immunosuppressive activity of the ganglioside is required. The compositions include gangliosides having ceramide moleties wherein the fatty acid portion is substantially enriched in carbon chains containing from 21 to 30 carbon atoms and less than 18 carbon atoms. Preferably, the compositions include gangliosides with terminal sialic acid groups and a low number of saccharide units. Ganglioside $G_{M4}$ is a preferred ganglioside for use in compositions of the present invention wherein the fatty acid portion of the $G_{M4}$ ganglioside has carbon chains containing less than 18 carbon atoms.

The above-discussed and many other features and attendant advantages of the present invention will become better understood by a reference to the following detailed description when taken in conjunction with the accompanying drawings.

BRIEF DESCRIPTION OF THE DRAWINGS

FIG. 3 is a diagrammatic representation showing the nomenclature which is used to describe the carbon chain structures of the long chain base and fatty acid portions of the ceramide moiety.

DETAILED DESCRIPTION OF THE INVENTION

The method of the present invention involves treating animals with gangliosides to suppress an immune response.

Figure 1:
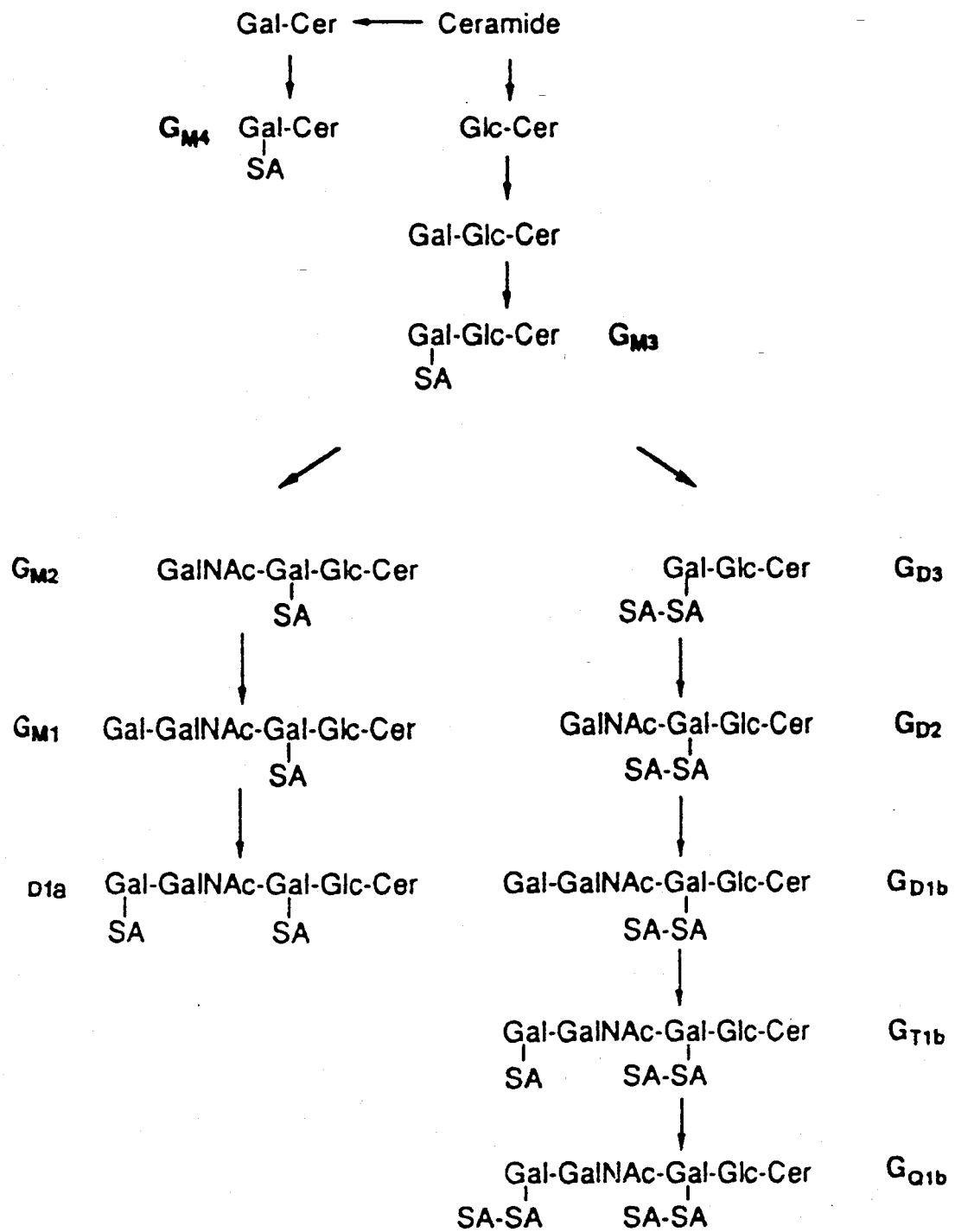
FIG. 1 is a schematic representation of the major human brain gangliosides showing their structure and proposed pathways of biosynthesis.
Figure 1:
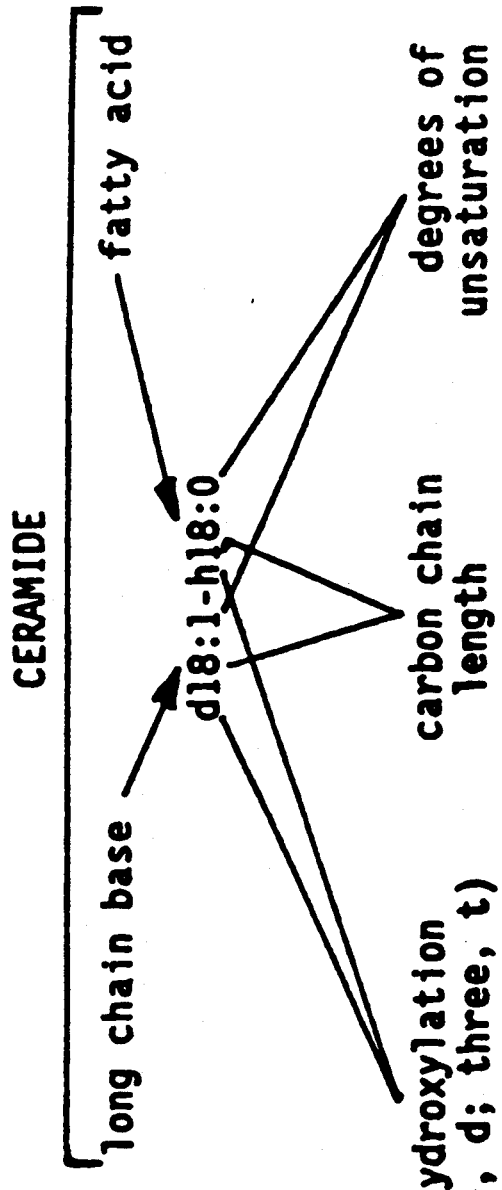

Ten common human brain gangliosides and their biosynthetic pathway are set forth in the FIG. 1. The structure of each ganglioside is set forth using conventional abbreviations for the ceramide, saccharide and sialic acid (SA) groups. The FIG. 1 also outlines the biosynthetic pathway of the gangliosides. The biosynthesis of gangliosides is discussed in detail in S. Roseman, Chem. Phys. Lipids, 5:270-297, 1970.

Figure 2:
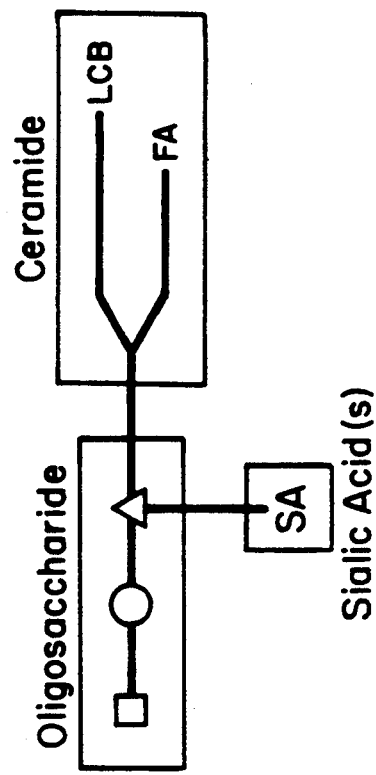
FIG. 2 is a schematic representation of ganglioside structure showing the basic oligosaccharide or carbohydrate moiety and the ceramide moiety.

As shown schematically in FIG. 2, the ganglioside molecule consists of three elements. The oligosaccharide or carbohydrate moiety or core to which is attached one or more sialic acids and a hydrophobic lipid (ceramide) structure which generally is embedded in the cell membrane. FIG. 3 sets forth the nomenclature which is used to describe the ceramide moiety. The ceramide moiety includes a long chain base (LCB) portion and a fatty acid (FA) portion. The number to the left of the colon indicates the carbon chain length of the fatty acid or long chain base, and the number to the right indicates the degree of unsaturation. The major long chain base structures (to the left of the dash) of normal human brain gangliosides are d18:1 and d20:1, and of extraneural gangliosides, d18:1. The major fatty acid structures (to the right of the dash) are 18:0 and 20:0.

In accordance with the present invention, it was discovered that the immunosuppressive activity of gangliosides is greater for gangliosides not of normal human brain origin, e.g. tumor gangliosides, and especially those gangliosides having fatty acid portions wherein the fatty acid portion comprises carbon chains having from 21 to 30 atoms and less than 18 carbon atoms. Further, it was also discovered that partial hydroxylation of the fatty acid i.e. α-hydroxylation of the fatty acyl group, decreases the immunosuppressive activity of the ganglioside.

The present invention has application to all 10 of the common human brain gangliosides identified in FIG. 1. In addition, the present invention has application to every other natural ganglioside and to other, synthetic, gangliosides. Whatever the carbohydrate structure, the choice or manipulation of ceramide (fatty acid) structure of the gangliosides in accordance with the present invention can alter immunosuppressive activity. The present invention involves increasing the immunosuppressive activity of these gangliosides by purifying or otherwise producing the gangliosides so that the length of the carbon chains in the fatty acid portion is less than 18 carbon atoms.

Gangliosides having a terminal sialic acid group are more effective as immunosuppressants than gangliosides with internally located sialic acids or desialylated gangliosides (NGSL's). Sialic acid groups are terminal when they are bound to the non-reducing end of the terminal monosaccharide which is located on the sugar moiety opposite the ceramide moiety. Exemplary gangliosides with terminal sialic acid groups include $G_{M4}$, $G_{M3}$, $G_{M1b}$, $G_{D1a}$, $G_{T1b}$, and $G_{Q1b}$ and sialosylparaglobosise (SPG). The terminal sialic acid groups can include up to ten and possibly more sialic acids. However, gangliosides with sialic acid groups having three or less sialic acids are preferred.

The present invention is particularly preferred for use with the above-identified gangliosides having terminal sialic acid groups. Preferably, substantially all of the fatty acid portions present in the ganglioside will have carbon chains with from 21 to 30 or less than 18 carbon atoms. In other words, it is particularly preferred to have gangliosides with ceramide structures having maximum heterogeneity wherein fatty acid portions having carbon chains with less than 18 carbon atoms and fatty acid portions with carbon chains of between 21 and 30 carbon atoms are combined in a single ganglioside mixture. Although it is possible to include gangliosides of the structure of those of normal human brain, having from 18 to 20 carbon atoms in the fatty acid portion, it is preferred that the proportion of fatty acids with carbon atoms between 21 and 30 and under 18 should be as large as possible to maximize the immunosuppressive activity of the particular ganglioside. Preferably, the ganglioside will contain over approximately 50% ceramide structures having less than 18 or from 21-30 carbon atoms in the fatty acid portion.

It was also discovered that, in accordance with the present invention, gangliosides in which the fatty acid portion includes ceramide structures having below 18 carbon atoms also demonstrated particularly increased immunosuppressive activity. Thus, the preferred ganglioside which is homogeneous in ceramide structure would have a fatty acid acyl group in which the carbon chain consists of less than 18 carbon atoms.

In accordance with the present invention, gangliosides are purified and isolated with respect to (i) their carbohydrate structure and (ii) their ceramide structure. Gangliosides are isolated to provide individual species wherein the fatty acid portion of the ceramide moiety contains carbon chains having less than 18 or from 21 to 30 carbon atoms. Purification and isolation of such gangliosides can be accomplished by a combination of normal phase and reversed-phase high pressure liquid chromatography (HPLC) as described by Ladisch et al. in the article entitled Aberrant Hydroxylation of Human Tumor Gangliosides, Journal of Biological Chemistry 264 12097-105, 1989.

The gangliosides which are purified to form mixtures having ceramide moieties in accordance with the present invention may be prepared according to known procedures. For example, the gangliosides may be prepared by known isolation procedures from brain or nervous system tissue, other normal tissues, body fluids, and abnormal (e.g., tumor) tissue. Alternatively, the gangliosides may be prepared synthetically by procedures such as those set forth in U.S. Pat. No. 4,868,292. The preferred gangliosides are those Kith sialic acid moieties made up of N-acetyl-neuraminic acid and/or N-glycolylneuraminic acid groups which are either unmodified (i.e., free acids) or easily convertible to these forms. Preferred saccharides for the carbohydrate moieties are glucose and galactose, alone or together with other suitable saccharides which include N-acetyl galactosamine, N-acetylglucosamine and fucose.

It was discovered that the immunosuppressive activity of gangliosides (i) is highest when the ganglioside contains a terminal sialic acid, and (ii) increases as the number of saccharides in the carbohydrate moiety is reduced. Accordingly, it is preferred that gangliosides with a lower number of saccharides and a terminal sialic acid be used. Preferably, the ganglioside will be a monosaccharide, such as $G_{M4}$.

Another preferred ganglioside is one which does not include a saccharide as part of the carbohydrate moiety, i.e. there is no neutral sugar moiety. The chemical name for this compound would be sialosylceramide. For the purposes of this specification, such gangliosides will be identified as $G_{M5}$. Synthesis of $G_{M5}$ ganglioside is disclosed in the previously mentioned U.S. Pat. No. 4,868,292. It is expected that $G_{M5}$ ganglioside will be as active as $G_{M4}$ with respect to in vivo immunosuppression.

Although the preferred ganglioside structures contain an unsubstituted terminal sialic acid, it will be obvious to those skilled in the art that any ganglioside molecule that can be metabolized in vivo to provide such structures which also include ceramide moieties having heterogeneous fatty acid portions with over 20 or under 18 carbon atoms are also within the scope of the present invention, as are gangliosides with homogeneous fatty acid portions containing under 18 carbon atoms. Such gangliosides, for example, include certain ganglioside lactones and similar substituted gangliosides. Preferably, the fatty acid will not be hydroxylated.

In accordance with the present invention, gangliosides with increased immunosuppressive activities include mixtures wherein the ceramide moiety includes heterogeneous fatty acid portions that are enriched in carbon chains of less than 18 carbon atoms or greater than 20 carbon atoms. The increase in heterogeneity provided by having fatty acids with carbon chains both greater than and less than those normally occurring in normal brain gangliosides (i.e. 18–20 carbon atoms) provides increased immunosuppressive activity over that of normal brain gangliosides. It is preferred that the relative amounts of fatty acid portions with carbon chain lengths below 18 carbon atoms be greater than the amount of longer chain fatty acids (i.e. greater than 20 carbon atoms) in the preferred ganglioside mixtures in accordance with the present invention. Finally, it is preferred that a ganglioside with a homogeneous ceramide structure contain a fatty acyl group of less than 18 carbon atoms.

Gangliosides may bind to plasma proteins and this binding reduces their effectiveness as an immunosuppressant due to competitive inhibition of binding to leukocytes. Accordingly, it is preferred that the gangliosides be introduced into the animal encapsulated in liposomes or packaged in resealed erythrocytes. This protective procedure will be described in detail below. Alternatively, when protection of the ganglioside from plasma protein binding is not possible, the preferred treatment procedure is to increase the dosage to minimize the neutralization effects caused by binding to plasma proteins.

In the present invention, the term "suppressive" denotes a lessening of the detrimental effect of the undesirable immune response in the animal receiving therapy. The term "immunosuppressively effective" means that the amount of ganglioside used is of sufficient quantity to suppress the cause of disease or symptoms due to the undesirable immune response. The term "animal" also denotes humans.

The dosage ranges for the administration of the gangliosides of the invention are those large enough to produce the desired effect in which the symptoms of the immune response show some degree of suppression. The dosage should not be so large as to cause adverse side effects. Generally, the dosage will vary with the age, condition, sex and extent of the disease in the animal and can be determined by one of skill in the art. The dosage can be adjusted by the individual physician in the event of any contraindications. Dosage can vary from less than 1 mg/kg/dose to about 100 mg/kg/dose, preferably about 5 mg/kg/dose to 10 mg/kg/dose, in one or more dose administrations daily.

The gangliosides of the invention can be administered parenterally by single injections or by gradual infusion over time. The gangliosides can be administered intravenously, intraperitoneally, intramuscularly, subcutaneously, intracavitarily, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils, intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Additional pharmaceutical methods may be employed to control the duration of action. Controlled release preparations may be achieved by the use of polymers to complex or adsorb the ganglioside. The controlled delivery may be exercised by selecting appropriate macromolecules (for example, polyesters, polyamino carboxymethylcellulose, and protamine sulfate) and the concentration of macromolecules as well as the methods of incorporation in order to control release. Another possible method to control the duration of action by controlled release preparations is to incorporate the ganglioside into particles of a polymeric material such as polyesters, polyamino acids, hydrogels, poly (lactic acid) or ethylene vinylacetate copolymers.

In order to protect the gangliosides from binding with plasma proteins, it is preferred that the gangliosides be entrapped in microcapsules prepared, for example, by coacervation techniques or by interfacial polymerization, for example, hydroxymethylcellulose or gelatin-microcapsules and poly (methymethacrylate) microcapsules, respectively, or in colloidal drug delivery systems, for example, liposomes, microspheres, microemulsions, and nonocapsules or in macroemulsions, or as micelies. Such teachings are disclosed in Remington's Pharmaceutical Sciences (16th Ed., A. Oslo, ed., Mack, Easton, Pa., 1980).

The gangliosides of the invention are well suited for use in targetable drug delivery systems such as synthetic or natural polymers in the form of macromolecular complexes, nanocapsules, microspheres, or beads, and lipid-based systems including oil-in-water emulsions, micelies, mixed micelies, liposomes, and resealed erythrocytes. These systems are known collectively as colloidal drug delivery systems. Typically, such colloidal particles containing the dispersed gangliosides are about 50 nm–2 μm in diameter. The size of the colloidal particles allows them to be administered intravenously such as by injection, or as an aerosol. Materials used in the preparation of colloidal systems are typically sterilizable via filter sterilization, nontoxic, and biodegradable, for example, ethylcellulose, casein, gelatin, lecithin, phospholipids, and soybean oil. Polymeric colloidal systems are prepared by a process similar to the coacervation of microencapsulation.

Most preferred as a targeted delivery system for the gangliosides of the invention are liposomes. When phospholipids are gently dispersed in aqueous media, they swell, hydrate, and spontaneously form multilamellar concentric bilayer vesicles with layers of aqueous media separating the lipid bilayer. Such systems are usually referred to as multilamellar liposomes or multilamellar vesicles (MLVs) and have diameters ranging from about 100 nm to about 4 μm. When MLVs are sonicated, small unilamellar vesicles (SUVs) with diameters in the range of from about 20 to about 50 nm are formed, which contain an aqueous solution in the core of the SUV.

The composition Of the liposome is usually a combination of phospholipids, particularly high-phase-transition-temperature phospholipids, usually in combination with steroids, especially cholesterol. Other phospholipids or other lipids may also be used.

Examples of lipids useful in liposome production include phosphatidyl compounds, such as phosphatidylglycerol, phosphatidylcholine, phosphatidylserine, and phosphatidylethanolamine. Particularly useful are diacylphosphatidylglycerols, where the lipid moiety contains from 14–18 carbon atoms, particularly from 16–18 carbon atoms, and are saturated. Illustrative phospholipids include egg phosphatidylcholine, dipalmitoylphosphatidylcholine, and distearoylphosphatidylcholine.

In preparing liposomes containing the gangliosides of the invention, such variables as the efficiency of ganglioside encapsulation, lability of the ganglioside, homogeneity and size of the resulting population of liposomes, ganglioside-to-lipid ratio, permeability instability of the preparation, and pharmaceutical acceptability of the formulation should be considered. Szoka, et al, *Annual Review of Biophysics and Bioengineering*, 9:467, 1980; Deamer, et al., in *Liposomes*, Marcel Dekker, New York, 1983, 27: Hope, et al., *Chem. Phys. Lipids*, 40:89, 1986).

The targeting of liposomes has been classified based on anatomical and mechanistic factors. Anatomical classification is based on the level of selectivity, for example, organ-specific, cell-specific, and organelle-specific. Mechanistic targeting can be further distinguished based upon whether it is passive or active. Passive targeting utilizes the natural tendency of liposomes to distribute to cells of the reticula-endothelial systems (RES) in organs which contain sinusoidal capillaries. Active targeting, on the other hand, involves the alteration of the liposome by coupling the liposome to a specific ligand such as a monoclonal antibody, sugar, glycolipid, or protein, or by changing the composition or size of the liposomes themselves in order to achieve targeting to organs and cell types other than the naturally occurring sites of localization. Alternatively, liposomes may physically localize in capillary beds such as the lung or may be given by site-specific injection.

Another targeted delivery system which can be used with the gangliosides of the invention is resealed erythrocytes. When erythrocytes are suspended in a hypotonic medium, swelling occurs and the cell membrane ruptures. As a consequence, pores are formed with diameters of approximately 200–500 Å which allow equilibration of the intracellular and extracellular environment. If the ionic strength of this surrounding media is then adjusted to isotonic conditions and the cells incubated at 37° C., the pores will close such that the erythrocyte reseals. This technique can be utilized with the gangliosides of the invention to entrap the ganglioside inside the resealed erythrocyte. The resealed erythrocyte containing the ganglioside can then be used for targeted delivery.

The targeted delivery system containing the gangliosides of the invention may be administered in a variety of ways to a host, particularly a mammalian host, such as intravenously, intramuscularly, subcutaneously, intra-peritoneally, intravascularly, topically, intracavitarily, transdermally, intranasally, and by inhalation. The concentration of the gangliosides will vary upon the particular application, the nature of the disease, the frequency of administration, or the like. The targeted delivery system-encapsulated ganglioside may be provided in a formulation comprising other compounds as appropriate and an aqueous physiologically acceptable medium, for example, saline, phosphate buffered saline, or the like.

The above disclosure generally describes the present invention. A further understanding can be obtained by reference to the following specific examples which are provided for purposes of illustration and are not intended to be limiting.

EXAMPLE 1

Preparation and Chemical Characterization of Human Brain Gangliosides

Normal human brain tissue was extracted with chloroform-methanol (Ledeen, et al., Methods Enzymol., 83:139–191, 1982) to yield a ganglioside-containing total lipid extract (TLE). The total ganglioside fractions were then purified by partitioning the TLE twice in the solvent mixture of diisopropylether, 1-butanol, and 0.3% aqueous NaCl (6:4:5) (Ladisch, et al., Anal. Biochem., 146:220–231, 1985). Salts and low molecular weight contaminants were removed from the lyophilized final lower aqueous phase by Sephadex G-50 size-exclusion chromatography using double distilled, deionized water as the mobile phase. The gangliosides were recovered in the void volume and lyophilized.

The purified mixture of total human brain gangliosides was separated by normal phase HPLC into individual ganglioside species differing in carbohydrate structure according to the method of Gazzotti, et al., J. Chromatogr., 348:371–378, 1985. 100 nmol portions of total brain ganglioside were chromatographed using the Perkin-Elmer Isopure HPLC system, at ambient temperature on a LiChrosorb-$NH_2$ column (250 mm length, 4 mm i.d., and 7 micron average particle diameter, Merck, Darmstadt, Germany). The elution program consisted of a gradient of the following solvent mixtures; acetonitrile-5 mM Sorensen's phosphate buffer (83:17), pH 5.6, and acetonitrile-20 mM Sorensen's phosphate buffer (1:1) pH 5.6. All solvents used are HPLC grade (Fisher Scientific). The elution profile was monitored by flow-through detection of UV absorbance at 215 nm (Perkin-Elmer LC 90 Bio UV detector). The ganglioside fractions were desalted by Sephadex G-50 size-exclusion chromatography. Nine brain ganglioside species were recovered in this way. They were $G_{M4}$, $G_{M3}$, $G_{M2}$, $G_{M1}$, $G_{D3}$, $G_{D1a}$, $G_{D1b}$, $G_{T1b}$, and $G_{Q1b}$. $G_{D2}$ was prepared by enzymatic ($\beta$-galactosidase) removal of the terminal galactose from $G_{D1b}$ and repurified by HPLC. The purified gangliosides were blanketed with nitrogen and stored under anhydrous conditions at $-20°$ C. The homogeneity of the fractions was verified by HPTLC.

Gangliosides were quantitated as nmol lipid-bound sialic acid (LBSA) by the modified calorimetric resorcinol assay (L. Svennerholm, Acta Chem. Scand., 12:547-554, 1958; Miettinen, et al., Acta Chemi. Scand., 13:856-858, 1959). To permit comparison of all data on a molecular basis, the resorcinol assay results are converted to nmol ganglioside by the formula:

$$\text{nmol ganglioside} = \frac{\text{nmol lipid-bound sialic acid measured}}{\text{no. of sialic acids/ganglioside molecule}}$$

In the case of $G_{T1b}$, for example, the divisor is 3.

Initial qualitative characterization of the gangliosides was achieved by high performance thin layer chromatography (HPTLC). $10 \times 20$ cm precoated Silica Gel-60 HPTLC plates (Merck, Darmstadt, Germany) which had been activated by desiccation in vacuo over sodium pentoxide were used. The plates were developed in chloroform:methanol:0.25% $CaCl_2 2H_2O$, 60:40:9. Gangliosides were visualized as purple bands with resorcinol-HCL reagent (L. Svennerholm, Biochim. Biophys. Acta, 24:604-611, 1957). Orcinol reagent was used to detect the desialylated (neutral) glycosphingolipids (L. Svennerholm, J. Neurochem., 1:42-53, 1956). The oligosaccharide structure of individual ganglioside molecular species was confirmed by negative-ion fast atom bombardment mass spectroscopy (FABMS) of the intact, underivatized ganglioside molecules (Ladisch, et al., J. Biol. Chem., 264:1209-1215, 1989).

EXAMPLE 2

Preparation and Chemical Characterization of Tumor Gangliosides

Tumor tissue or tumor cells which have been propagated in vitro are purified using the same methodology described for the purification of human brain gangliosides as described in Example 1 above. Following total lipid extraction, the solvent partition step, and normal phase HPLC, individual gangliosides homogeneous in carbohydrate structure are obtained. The oligosaccharide structure of the individual species was confirmed by negative ion FABMS, as in Example 1. This procedure, then, results in gangliosides identical to those prepared in Example 1 in carbohydrate structure, but differing in ceramide structure. For example, whereas $G_{D2}$ ganglioside obtained using human brain tissue as the source contains fatty acids in the ceramide portion which predominantly have carbon chain lengths of 18 and 20, $G_{D2}$ isolated from tumor cells (neuroblastoma) has a much more heterogeneous mixture of ceramide structures, with a predominance of fatty acids containing more than 20 and less than 18 carbon atoms. Likewise, comparing $G_{M2}$ of human brain with $G_{M2}$ of human tumor tissue reveals a striking heterogeneity of ceramide structure in the latter (Ladisch et al., J. Biol. Chem. 264: 1209-1215, 1989). These striking differences in ceramide structure, as is set forth in the examples below, result in marked differences in immunosuppressive activity.

EXAMPLE 3

Isolation of Ceramide Species of Individual Gangliosides by Reversed Phase HPLC

Since the only structural difference in gangliosides isolated from human brain and from tumors or tumor cells by the methods described in examples 1 and 2 lie in the ceramide portion of the molecule, gangliosides which were already homogeneous in their carbohydrate structure (e.g., $G_{D2}$, $G_{M2}$, etc.) were further purified by reversed-phase HPLC to obtain gangliosides also homogeneous in ceramide structure. That is, the above isolated gangliosides were further purified to separate them into gangliosides having ceramide structures with fatty acid portions ranging in carbon atom length from C16 to C24. The gangliosides which were purified and separated with respect to ceramide structure were $G_{D2}$, $G_{M2}$, $G_{M1b}$, $G_{M3}$ and SPG. The procedure for purifying the various gangliosides to homogeneity according to ceramide structure was as follows:

Fractions of each ganglioside that were homogeneous in the oligosaccharide moiety were further separated to yield individual molecular species of different ceramide structure by reversed-phase HPLC. Ten nmol of ganglioside in 25$\mu$ of HPLC water were loaded in the same injector and separated by the same HPLC system described above, using a reversed-phase Hibar RT Lichrosorb Si 100 RP-8 column (5$\mu$ particle size, 4.6 mm inside diameter, 25 cm length, Merck, Darmstadt, Germany). Chromatography of the total ganglioside mixture was carried out at ambient temperature with the solvent system of acetonitrile and 5 mM sodium phosphate buffer, pH 7.0. The specific details of the solvent ratios and their change with time (elution program) and the flow rate were adjusted to optimize the purification of each individual ganglioside. To give an example, to separate $G_{M2}$ into its individual species of different ceramide structure, the buffer system was maintained at an acetonitrile: phosphate buffer ratio of 1:1 for the first 8 min, linearly increased to 3:2 for the next 6 min, and finally kept at 3:2 for the remainder (36 min) of the 50-min program. The flow rate was 0.5 ml/min. The program was varied as necessary according to the carbohydrate structure of the particular ganglioside being purified. The elution profile was monitored by flow-through detection at a wavelength of 195 nm. The eluting gangliosides were collected, lyophilized, and desalted by Sephadex G-50 gel filtration.

Gangliosides prepared in this manner were then characterized by FABMS as in examples 1 and 2. These studies confirmed complete molecular homogeneity (i.e., of both carbohydrate and ceramide portions of the molecule) as well as providing data by which the complete structure could be identified.

EXAMPLE 4

Increased Immunosuppressive Activity of Individual Gangliosides is Associated with Ceramide Composition More Heterogeneous than that of Human Brain Gangliosides To determine the effect of ceramide structure upon immunosuppressive activity it is necessary to ensure that the molecules being studied are identical in carbohydrate structure. This was accomplished using the methods described in Examples 1, 2 and 3. This approach resulted in a series of pairs of molecules which could be compared for activity. For example, $G_{D2}$ ganglioside from human brain and tumor tissue, as well as $G_{D3}$ from these same sources, were studied with the results being shown in FIG. 4.

Figure 4:
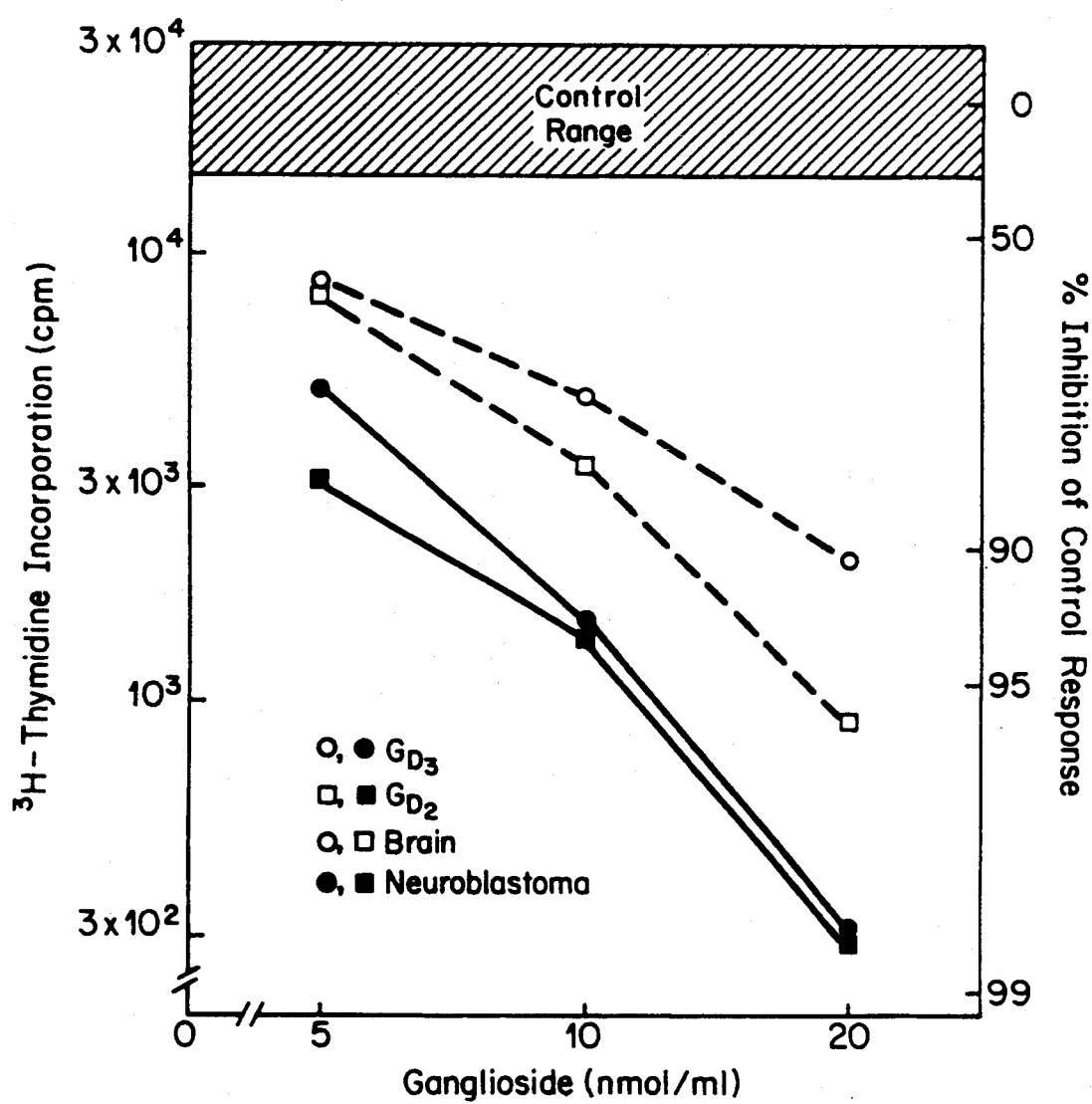
FIG. 4 is a graphic representation showing the increased immunosuppressive activity of tumor derived gangliosides $G_{D2}$ and $G_{D3}$.

FIG. 4 depicts the inhibition of tetanus-toxoid induced lymphoproliferative responses by human tumor gangliosides. $G_{D3}$ and $G_{D2}$, isolated from human brain or neuroblastoma tumor as indicated, were tested for their inhibitory effect on the tetanus-toxoid induced human lymphoproliferative response. Each point represents the mean of triplicate cultures, and this experiment is representative of 3 separate experiments.

The tests were conducted as follows:

The inhibition of the proliferative response of peripheral blood mononuclear cells (PBMC) represents a method by which the immunosuppressive activity of gangliosides can be determined. Inhibition of the proliferative response of PBMC by a given ganglioside or group of gangliosides is measured by determining thymidine uptake of stimulated cells.

Normal human peripheral blood mononuclear cells (PBMC) for use in the lymphocyte proliferation assays were isolated by Ficoll-hypaque density gradient centrifugation (A. Boyum, Scand. J. Clin. Lab. Invest., 21:77-89, 1968) from whole blood collected in preservative-free heparin (50 U/ml). The cells were washed three times and resuspended in complete serum-free HB104 medium supplemented with 2 mM L-glutamine, 2 mM sodium pyruvate, 1% HB104 protein supplement (albumin, insulin, and transferrin; Hana Biologics), 10 mM HEPES buffer solution to assist in hP control, and autologous human plasma added to a final concentration of 0.5%. This medium allows assays to be conducted in low plasma concentrations without loss of PBMC viability and with preservation of PBMC proliferative responses when the plating is completed expeditiously.

To enhance the usefulness of this method, the total culture volume was reduced by three-fourths over that of a standard assay system by using 96-well half area (A/2) tissue culture clusters (Costar #3696). The problem of evaporation that can occur in these small wells over the course of a 6-day incubation period (particularly in the peripheral wells of the plates) was avoided by using only the center 60 of the 96 wells of each plate and filling the interwell compartments and unused wells with sterile distilled water.

To prepare the cultures (45 μl total volume), first 10 μl ganglioside solution was added/well. Then the PBMC suspension (25 μl, $2 \times 10^6$ cells/ml complete medium) was added, and PBMC and gangliosides preincubated for 3 hours at 37° C. Finally, 10 μl of the previously determined optimal concentration of the stimulant of lymphoproliferation was added (3.5 Lf/ml basal medium, in the case of tetanus toxoid (Mass. Dept. of Health, Boston, Mass.). An equal volume of basal medium alone was added to the unstimulated (control) cultures.

The complete cultures were incubated at 37° C. in 95% air/5% $CO_2$. The culture duration is 3 days when the stimulant is a non-specific mitogen (PHA, ConA, PWM) and 6 days to assess antigen-specific responses (tetanus and diphtheria toxoids, candida antigen) (Ladisch, et al., J. Clin. Invest., 74:2074-2081, 1984). At the end of the culture period, 0.5μ Ci $^3$H-thymidine in 50 μl medium was added to each well and the cultures incubated for an additional 4.5 hours. The cultures were harvested onto glass fiber filter paper and cellular uptake of $^3$H-thymidine uptake in stimulated cultures is determined by subtracting the mean cpm of unstimulated cultures. Percent inhibition is calculated by comparing the mean net $^3$H-thymidine uptake of cultures containing gangliosides with that of cultures without gangliosides.

$G_{D2}$ and $G_{D3}$ gangliosides were also isolated from tumors according to the same procedure used to isolate brain $G_{D2}$ gangliosides. The brain $G_{D2}$ and $G_{D3}$ gangliosides were determined to be composed substantially of ceramide moieties having fatty acid portions with 18-20 carbon atoms. The tumor $G_{D2}$ and $G_{D3}$ were found to be heterogenous with respect to the ceramide moiety. The majority (over 50 percent) of ceramide moieties had fatty acid portions which were below or above 18-20 carbon atoms, i.e. less than 18 and between 22-30.

FIG. 4 shows that both $G_{D3}$ and $G_{D2}$ are potent immunosuppressive molecules, and have similar marked inhibitory activity at concentrations of greater than 10 μM not caused by non-specific cytotoxicity. As can be seen from the results, human brain-derived gangliosides were much less inhibitory than neuroblastoma tumor gangliosides of proven identical oligosaccharide structure. For example, while 5 μM $G_{D3}$ isolated from human brain caused approximately 75% inhibition, 5 μM tumor-derived $G_{D3}$ caused fully 93% inhibition.

Numerous additional experiments, with a large variety of gangliosides of different carbohydrate structure, all confirm that gangliosides isolated from tumor sources and having greater ceramide heterogeneity than normal brain-derived gangliosides, were consistently more active in suppressing the normal human cellular immune response in vitro. The results of these experiments are set forth in Table 1. These examples show evidence that differences in ceramide structure are significant factors modulating immunosuppressive activity of gangliosides.

TABLE 1

Immunosuppressive Activity of a Series of Gangliosides Homogeneous in Carbohydrate Structure

| Carbohydrate Structure | Ganglioside Source | |
|---|---|---|
| | Normal Brain | Tumor Tissue |
| $G_{M2}$ | 19.7$^a$ (6)$^b$ | 0.1 (99) |
| $G_{M1}$ | 5.4 (74) | <0.1 (>99) |
| $G_{D3}$ | 6.1 (71) | <0.1 (>99) |
| $G_{D2}$ | 7.1 (66) | 4.5 (78) |
| $G_{D1b}$ | 4.0 (81) | <0.1 (>99) |
| $G_{T1b}$ | 5.0 (76) | 2.7 (87) |

$^a$net cpm $\times 10^{-3}$; control 20.9 $\times 10^3$ cpm
$^b$( ) = % inhibition; ganglioside concentration 2.5 μM The inhibitory activity of brain and tumor gangliosides was also compared for the gangliosides $G_{D1b}$ and $G_{M1}$. For each of these gangliosides, the normal brain gangliosides had ceramide moieties with fatty acids having 18-20 carbon atoms. The tumor gangliosides, like tumor derived $G_{D2}$, had a majority (over 50 percent) of ceramide moieties with fatty acid portions containing less than 18 or greater than 20 and above carbon atoms. The results of these comparative studies confirmed that the gangliosides in accordance with the present invention are significantly more immunosuppressive than normal brain gangliosides which contain ceramide moieties with predominantly 18-20 carbon atoms in the fatty acid portion.

EXAMPLE 5

Increased Immunosuppressive Activity of Homogeneous Individual Gangliosides is Associated with Shorter Fatty Acid Carbon Chain Length of the Ceramide $G_{D2}$ ganglioside obtained from neuroblastoma tumor cells was isolated according to the above procedure described in Example 3 into four different species of different ceramide structure having fatty acid carbon chain lengths of 16, 18, 22 and 24. The immunosuppressive activity of these four ganglioside fractions was compared by measuring the inhibition of the normal human lymphoproliferative response. A summary of the comparative inhibition of the various homogeneous ceramide fractions is set forth in FIG. 5.

Figure 5:
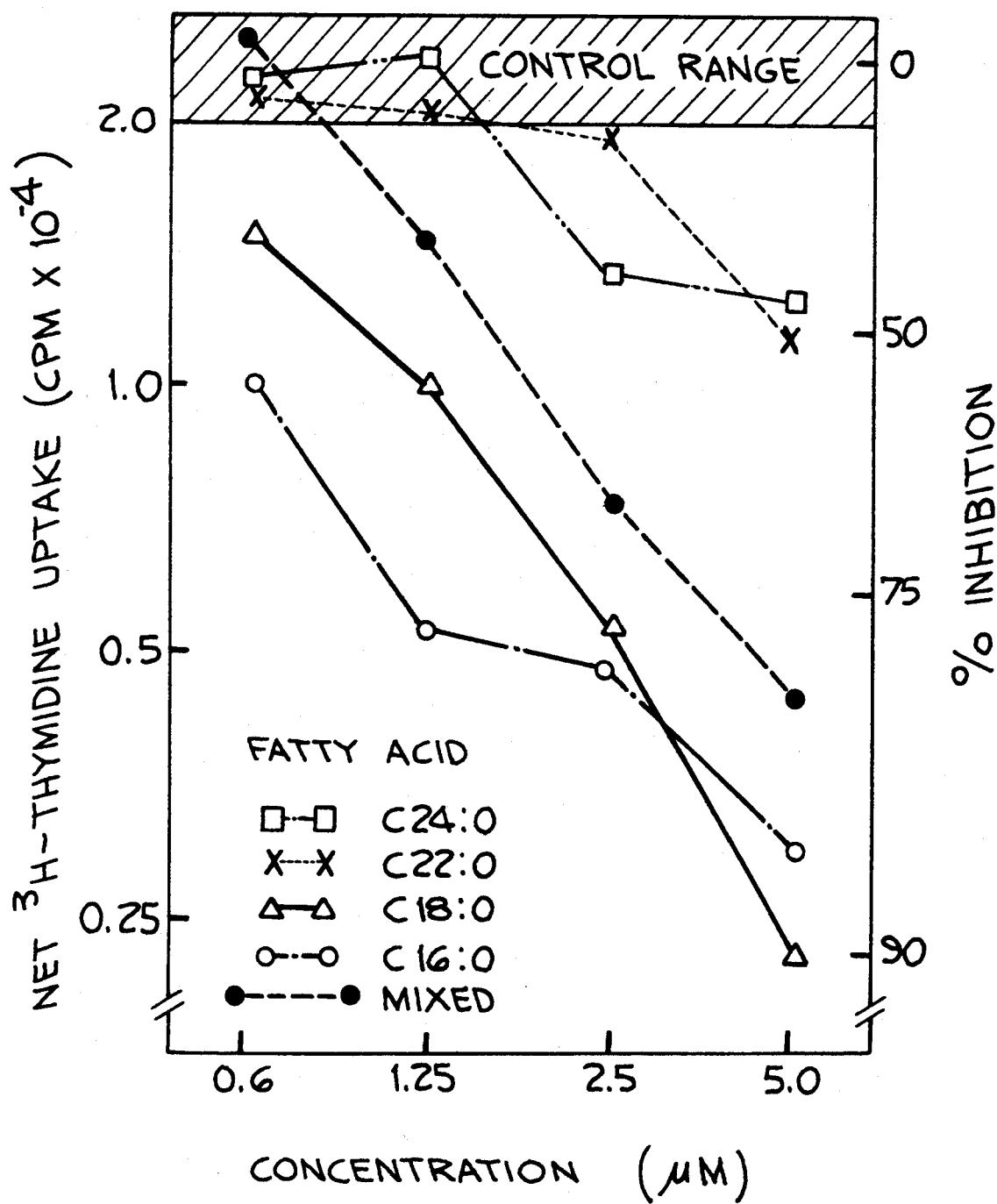
FIG. 5 is a graphic representation showing the increased immunosuppressive activity of $G_{D2}$ with homogeneous fatty acid groups having 18 or less carbon atoms.

As can be seen from FIG. 5, the $G_{D2}$ gangliosides with ceramide moieties having fatty acid with 16 or 18 carbon atoms was much more effective than either the 22 or 24 carbon fatty acid fractions or the total $G_{D2}$ ganglioside from which they were derived.

Figure 6:
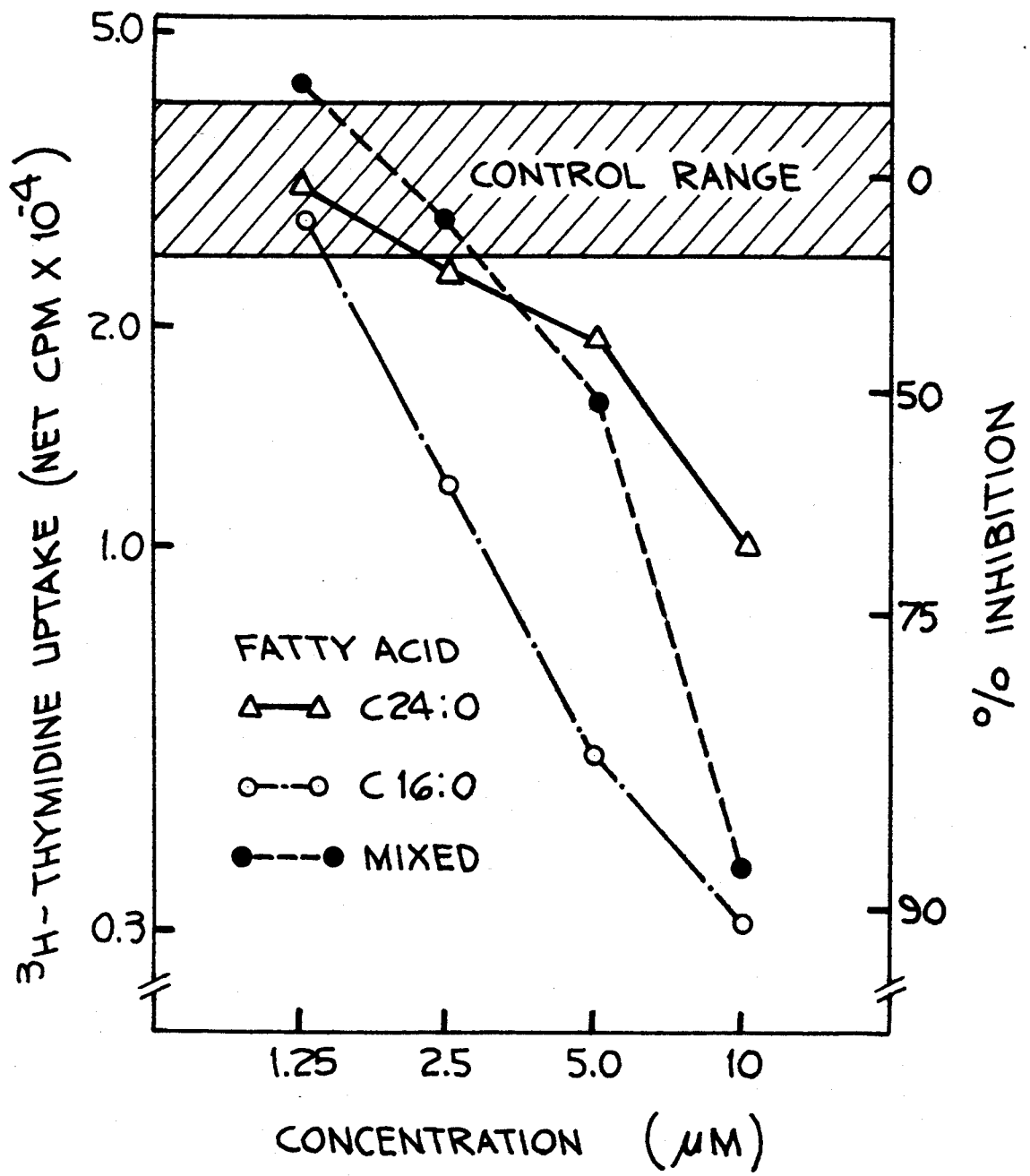
FIG. 6 is a graphic representation showing the increased immunosuppressive activity of $G_{M3}$ with fatty acid groups having less than 18 carbon atoms.
Figure 7:
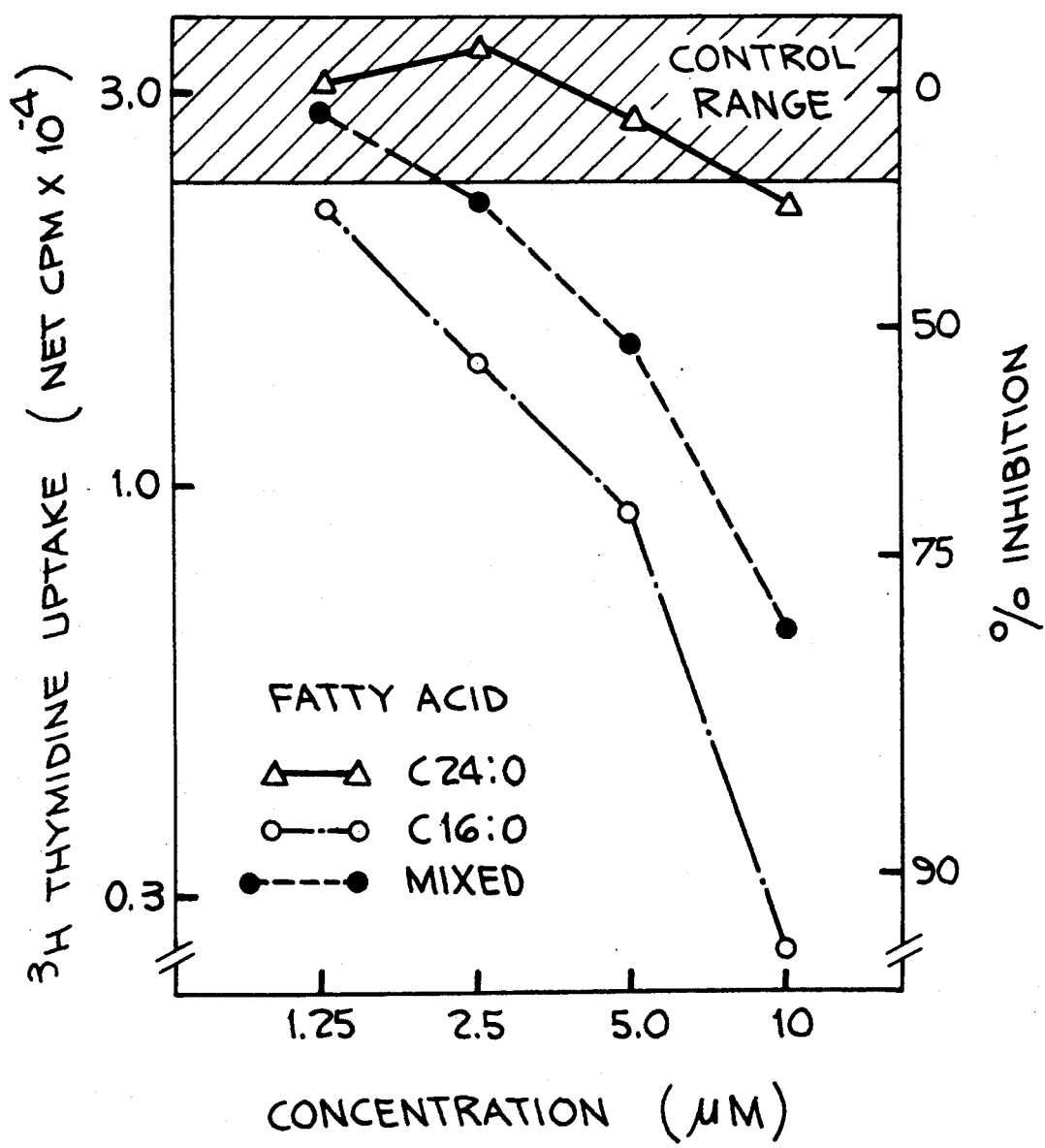
FIG. 7 is a graphic representation showing the increased immunosuppressive activity of SPG having fatty acid groups with less than 18 carbon atoms.

Similar examples were conducted using the ceramide species isolated from two other terminal sialic acid-containing gangliosides, $G_{M3}$ and SPG. In each of these cases the ganglioside having a ceramide containing a shorter fatty acyl group (16:0) was significantly more immunosuppressive than gangliosides of the same carbohydrate structure having a ceramide containing a longer chain fatty acyl group (24:0), or the carbohydrate-homogeneous, ceramide-heterogeneous ganglioside from which they were derived. In each case the original ganglioside from which the ceramide species were isolated and purified had activity lying in between that of the most and least active ceramide species derived from it. It is preferred that the gangliosides are purified to absolute homogeneity (or synthesized as a homogeneous molecule), because this allows the highest specific activity of gangliosides to be attained. The results of the tests on $G_{M3}$ and SPG are shown in FIGS. 6 and 7, respectively.

EXAMPLE 6

Figure 8:
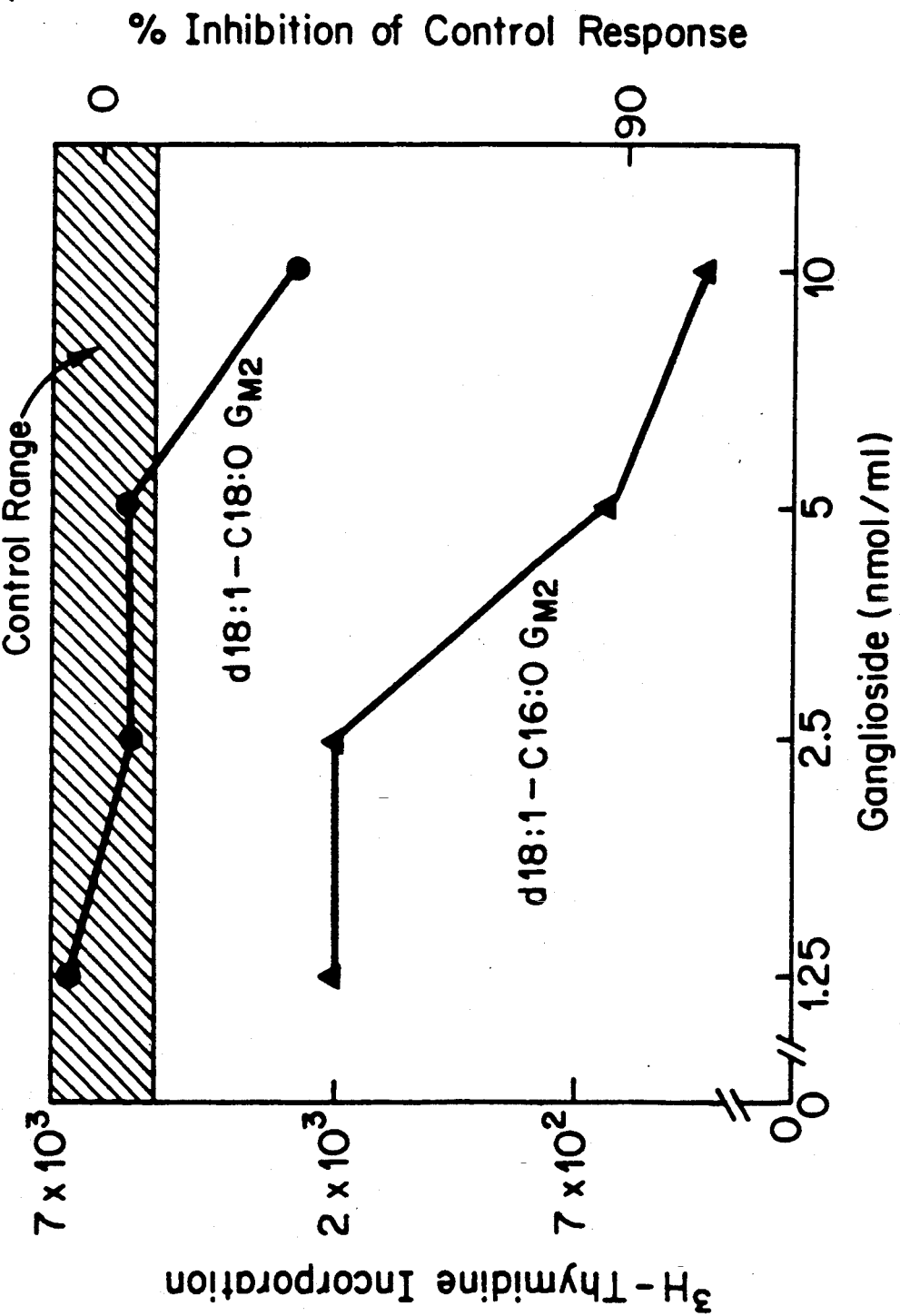
FIG. 8 is a graphic representation showing the increased immunosuppressive activity of $G_{M2}$ with a fatty acid portion having less than 18 carbon atoms.
Figure 9:
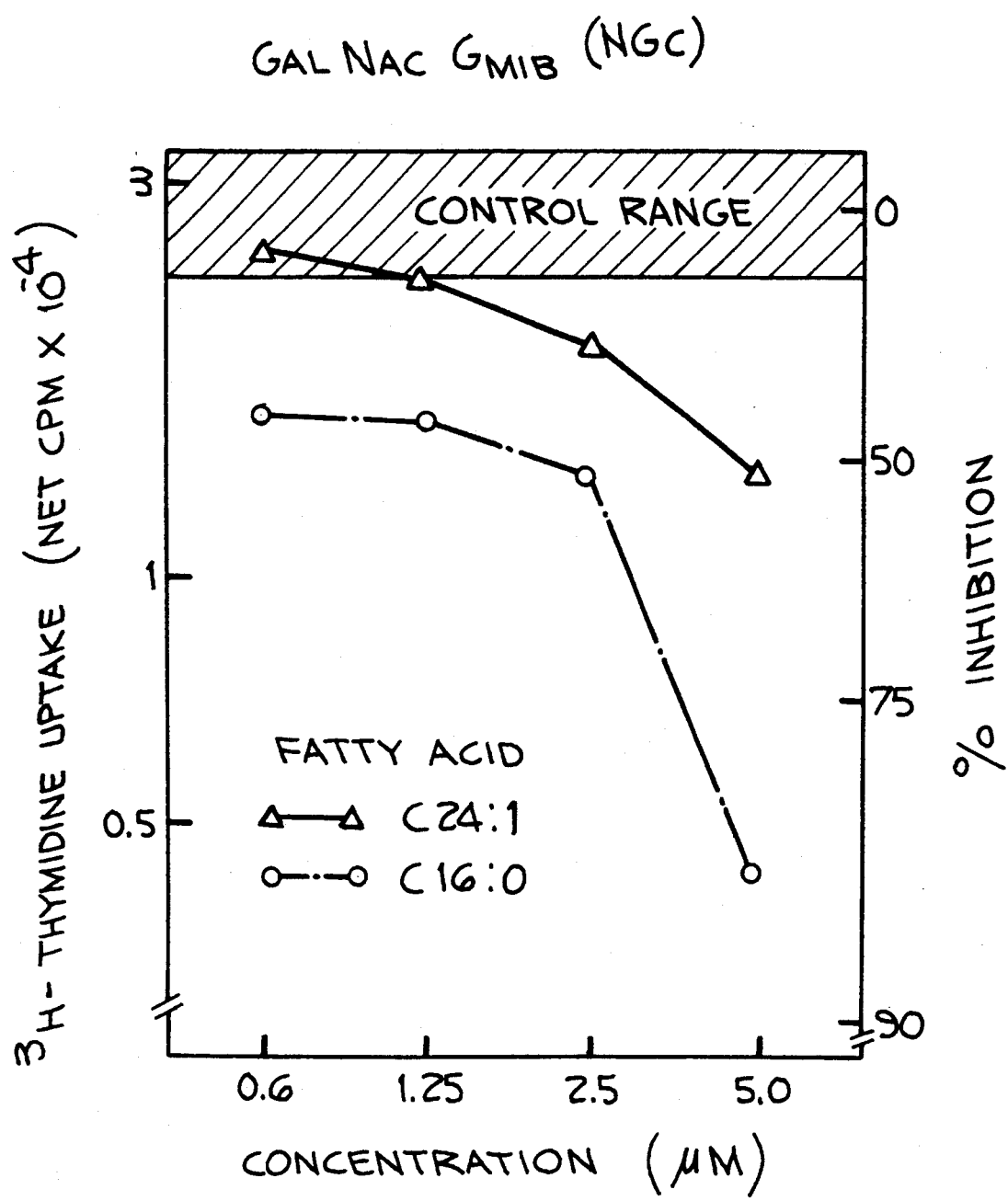
FIG. 9 is a graphic representation showing the increased immunosuppressive activity of Gal-NacG$_{m1b}$NGc with a fatty acid portion having 16 carbon atoms.

The significant effect of a shorter versus a long fatty acyl group in the ceramide of a ganglioside is not confined to gangliosides containing terminal sialic acids. This is seen by measurement of the immunosuppressive activity of two ceramide species of ganglioside (C16:0 vs. C18:0) and two ceramide species of GalNacG$_{M1b}$ ganglioside, (C16:0 vs. C24:1). FIGS. 8 and 9 show the results of the comparisons for $G_{M2}$ and GalNacG$_{M1b}$, respectively.

As is apparent from this example, independent of the nature of the rest of the molecular structure of a ganglioside (i.e., the carbohydrate portion), shorter fatty acyl chain lengths are associated with greater immunosuppressive activity than are longer fatty acyl chain lengths.

EXAMPLE 7

To further characterize the role of fatty acid structure of the ceramides upon immunosuppressive activity of a ganglioside, two highly purified gangliosides of fully defined structure were compared. These two gangliosides d18:1-C18:0 $G_{M2}$ and d18:1-hC18:0 $G_{M2}$, differed only in alpha-hydroxylation of the fatty acid in the latter species. The ganglioside which contained hydroxylated fatty acid was less immunosuppressive than the non-hydroxylated species. Therefore, it is preferable, for the purpose of causing immunosuppression that a ganglioside not contain a hydroxylated fatty acid. The results demonstrating the decrease in immunosuppression due to hydroxylation are set forth in Table 2.

TABLE 2

Effect of Fatty Acyl Hydroxylation upon Ganglioside Immunosuppressive Activity

| Ganglioside Concentration ($\mu M$) | $G_{M2}$ Ceramide Structure | |
|---|---|---|
| | d18:1-C18:0 | d18:1-hC18:0 |
| 2.5 | 11.3$^a$ (31)$^b$ | 16.7 (NI) |
| 5 | 8.6 (47) | 11.4 (30) |
| 10 | 2.3 (86) | 12.9 (21) |

$^a$cpm $\times 10^{-3}$; mean control cpm = 16.3 $\times 10^3$ cpm
$^b$( ) = % inhibition; NI = not inhibitory Those skilled in thee art will recognize, or be able to ascertain using no more than routine experimentation, many equivalents to the specific embodiments of the invention specifically described herein. Such equivalents are intended to be encompassed within the spirit and scope of the following claims.

What is claimed is:

1. A composition for suppressing an immune response comprising:
    a mixture of gangliosides which is more heterogeneous than human brain gangliosides, and/or which consists essentially of gangliosides having a carbohydrate moiety and a ceramide moiety, said ceramide moiety consisting of a long chain base portion and a fatty acid portion, wherein the majority of the fatty acid portions of the gangliosides in said mixture consist of a carbon chain having less than 18 carbon atoms; and
    a physiologically acceptable carrier for said mixture of gangliosides.

2. A composition for suppressing an immune response according to claim 1 wherein said fatty acid portion is not hydroxylated.

3. A composition for suppressing an immune response according to claim 1 wherein said gangliosides are encapsulated in liposomes.

4. A composition for suppressing an immune response according to claim 1 wherein said gangliosides are packaged in resealed erythrocytes.

5. A composition for suppressing an immune response according to claim 1 wherein the carbohydrate moiety for the gangliosides comprising less than 18 carbon atoms consists of a sugar moiety and a sialic moiety and wherein said sialic acid moiety comprises a terminal sialic acid group.

6. A composition for suppressing an immune response according to claim 5 wherein said sialic acid moiety consists of a a N-acetyl-neuraminic acid or N-glycolyl-neuraminimic acid.

7. A composition for suppressing an immune response according to claim 5 wherein said sugar moiety consists of saccharides selected from the group of saccharides consisting of glucose and galactose.

8. A composition for suppressing an immune response according to claim 5 wherein said sugar moiety consists of one saccharide.

* * * * *